(12) United States Patent
Gorecki

(10) Patent No.: US 6,278,523 B1
(45) Date of Patent: Aug. 21, 2001

(54) OPTICAL SENSOR ON A SILICON SUBSTRATE AND APPLICATION FOR THE IN SITU MEASUREMENT OF A FLUORESCENT MARKER IN THE SMALL BRONCHIA

(75) Inventor: Christophe Gorecki, Paris (FR)

(73) Assignee: Centre National de la Recherche Scientifique-CNRS (FR)

( * ) Notice: Subject to any disclaimer, the term of this patent is extended or adjusted under 35 U.S.C. 154(b) by 0 days.

(21) Appl. No.: 09/023,514

(22) Filed: Feb. 13, 1998

(51) Int. Cl.[7] ........................................ G01B 9/02
(52) U.S. Cl. ................................ 356/450; 356/513
(58) Field of Search ........................... 356/450, 512, 356/513, 514

(56) References Cited

U.S. PATENT DOCUMENTS 5,465,151  *  11/1995  WyBourne et al. .
5,854,868  *  12/1998  Yoshimora et al. .

* cited by examiner

*Primary Examiner*—Robert Kim
(74) *Attorney, Agent, or Firm*—Schnader Harrison Segal & Lewis LLP

(57) ABSTRACT

The sensor measures diffusion of a fluorescent marker in cavities. The sensor has a Mach-Zehnder micro-interferometer having a reference arm and a measurement arm. The reference arm has a deposit of a sensitive layer whose refractive index is modified when the sensitive layer is in contact with the fluorescent marker. In one embodiment, the micro-interferometer has a diode laser configured to generate a source beam, a substrate of silicon micro-machined with two Y junctions, where a first Y junction is configured to divide the source beam into a measurement beam along the measurement arm and a reference beam along the reference arm, a piezo-electric transducer configured to shift the frequency of the reference beam in phase by an acoustic modulation, wherein a second Y junction combines the measurement bean and the shifted reference beam to generate a combined beam; and a photo-detector configured to detect the combined beam. In one application, the sensor is used for in situ assessment of bronchial capillary permeability.

16 Claims, 5 Drawing Sheets

OPTICAL SENSOR ON A SILICON SUBSTRATE AND APPLICATION FOR THE IN SITU MEASUREMENT OF A FLUORESCENT MARKER IN THE SMALL BRONCHIA

BACKGROUND OF THE INVENTION

1. Field of the Invention

This invention relates to the field of miniaturised optical sensors and more particularly sensors intended for the measurement of a fluorescent marker in small cavities, for example, the small bronchia, for the in vivo measurement of bronchial capillary permeability.

2. Description of the Related Art

The use of an interferometric heterodyne probe, integrated onto silicon, is known in the state of the technology of miniaturisable optical sensors, notably in biomedical applications.

The principle of heterodyne technology in interferometry is based on the modification of the optical frequency on one of the arms of the interferometer. The interference fringes can be modulated in phase and detected photo-electrically. The technique allows access to the phase of the phenomenon observed directly from the optical signal. In comparison with homodyning techniques, that link counting of fringes to methods of linear interpolation, heterodyne detection has two main advantages:

an improvement of the resolution linked to the phase extraction, better tolerance of low frequency noise thanks to the shift of the useful signal far form external parasite signals.

The transposition of the massive architecture of heterodyne interferometry into a fibre version leads, in general, to a degradation of the signal to noise ratio, linked to external interference and parasitic reflections. In addition, "all fibre" shift devices are rare and one comes up against problems of coupling the massive phase modulators and the input of the fibre that seriously limit the applications that require miniaturisation of the probe.

Thanks to the optical technologies for integration onto silicon, the future is assured for micro-interferometers of very small size that can be manufactured by monolithic integration. The optical device integrated onto silicon is particularly well suited to "biomedical sensor" applications where a sensitive "superstrate" layer of hydrocarbon or polymer is deposited on the measurement arm of the interferometer (generally the Mach-Zehnder configuration). Some typical examples of biological and chemical sensors are described in the following documents:

"Integrated optical gas sensors using organically modified silicates as sensitive films", Sensors and Actuators B, Vol. 11, (1993), pp. 361–374, 4. A. Brandenburg, R. Edelhauser, F. Hutter.

"Integrated optical sensors for halogenated and non-halogenated hydrocarbons", Sensors for Actuators B, Vol. 11,(1993), pp. 207–212, G. Gauglitz, J. Ingenhoff.

"Influence of thin superstrate films on evanescent waves in surface waveguides", Ber. Bunsenges. Phys. Chem, Vol. 11, (1991), pp. 1588–1563, G. Gauglitz, J. Ingenhoff, "Integrated optical chemical and direct biochemical sensors", Sensors and Actuators B, Vol. 29, (1995), pp. 37–50.

"Integrated optics with macro-flow cell", Proc. SPIE, Vol. 1793, (1992), pp. 199–211, A. A. Boiarski, J. R. Busch, B. S. Bhullar, R. W. Ridgway, V. E. Wood.

If numerous integrated optical "bio-sensors" have appeared, they are based principally on homodyning technologies. The technique of integration of optical microprobes comes up against the difficulty of producing a modulation of the reference beam necessary for heterodyning onto a silicon substrate that is playing a passive role.

SUMMARY OF THE INVENTION

This invention is aimed at remedying this disadvantage by proposing an original optical architecture, notably for a specific "biomedical sensor" application. This architecture opens up a new route of carrying out the heterodyning technique based on an "active" arrangement, provided thanks to the interaction between an optical beam being propagated in a monomodal silicon guide and a surface acoustic wave. The piezo-electric material required for the generation of acoustic waves is a thin layer of zinc oxide.

The invention is also aimed at a particular application for such a sensor for the in vivo assessment of the permeability of the capillary walls in the small bronchia. Neither a method nor a device exists in the prior art that permits the in vivo assessment of the permeability of the capillary walls in the small bronchia.

The invention responds to this need by a method and a device that allows the in situ measurement of a fluorescent marker by an interferometric sensor, integrated onto a silicon substrate. Such a micro-optical-electrical-mechanical device is capable of providing a miniature measurement tool in the medical field, that can operate remotely, in situ and in vivo.

The usefulness of concentrating the measurement on the small bronchia rather than on the air cells, that is to say of measuring, in vivo the bronchial capillary permeability is that it allows quantification of the inflammation essentially within bronchia of diameter between 0.5 and 3 mm. In effect, these bronchia are the seat of an oedema through an increase in the permeability of the capillary walls in numerous inflammatory pathologies including asthma. Two aspects of the bronchial capillary permeability can be studied: the permeability to liquids and the permeability of a fluorescent indicator. The current techniques only permit measurement of the permeability of the capillaries on an isolated bronchus. Hence the permeability to liquids is assessed form the lowering of concentration of a non-diffusible fluorescent indicator as a function of time, when a hyperosmolar liquid is introduced into the bronchial opening. For the permeability to solutes, the passage of an indicator perfused into the bronchial opening towards the bronchial epithelium is measured.

BRIEF DESCRIPTION OF THE DRAWINGS

This invention will be better understood on reading the description which follows.

DETAILED DESCRIPTION

The sensor according to the invention makes use of a heterodyning interferometric probe integrated onto silicon.

The method of measurement according to the invention is based on the application to the small bronchia of a bronchial alveolar washing which is a technique currently used clinically, in the consulting room or at the patient's bedside in order to sample the liquid which lines the bronchia and the air cells in the physiological condition. A standard bronchial alveolar washing requires the introduction of a fibroscope into the distal airways, the installation of physiological salt solution, followed by reaspiration, this operation being repeated four or five times. Cell numeration and measurement so the concentrations of chemical substances, hormonal or pharmacological are then carried out on the samples of reaspired liquid. This analysis, applied to the measurement of the capillary and alveolar permeability permits an evaluation and provides a quantification of the pulmonary inflammation especially at the alveolar level.

The objective of the invention is to measure the bronchial capillary permeability. The usefulness of this measurement is to provide a quantification of the inflammation, above all at the level of the bronchia with a diameter of between 0.5 and 3 mm. In effect they are the seat of an oedema through the increase of permeability in numerous allergic inflammatory pathologies, such as asthma, and in infectious pathologies. In practice, if it is preceded by saturation of the region with a washing liquid, a continuous measurement of the diffusion of a fluorescent indicator from the wall to the bronchial opening where the sensor is situated should allow us to develop a quantification of the permeability. Other biological applications, both pharmacological and medical, are possible, given the possibility of fixing fluorochromes on the ions and numerous proteins. It is only possible for this project to be carried out with a measurement of the fluorescence in bronchia with a diameter smaller than those to which the fibroscope currently allows access, from which stems the interest in making available a miniaturised fluorescence sensor.

Figure 1:
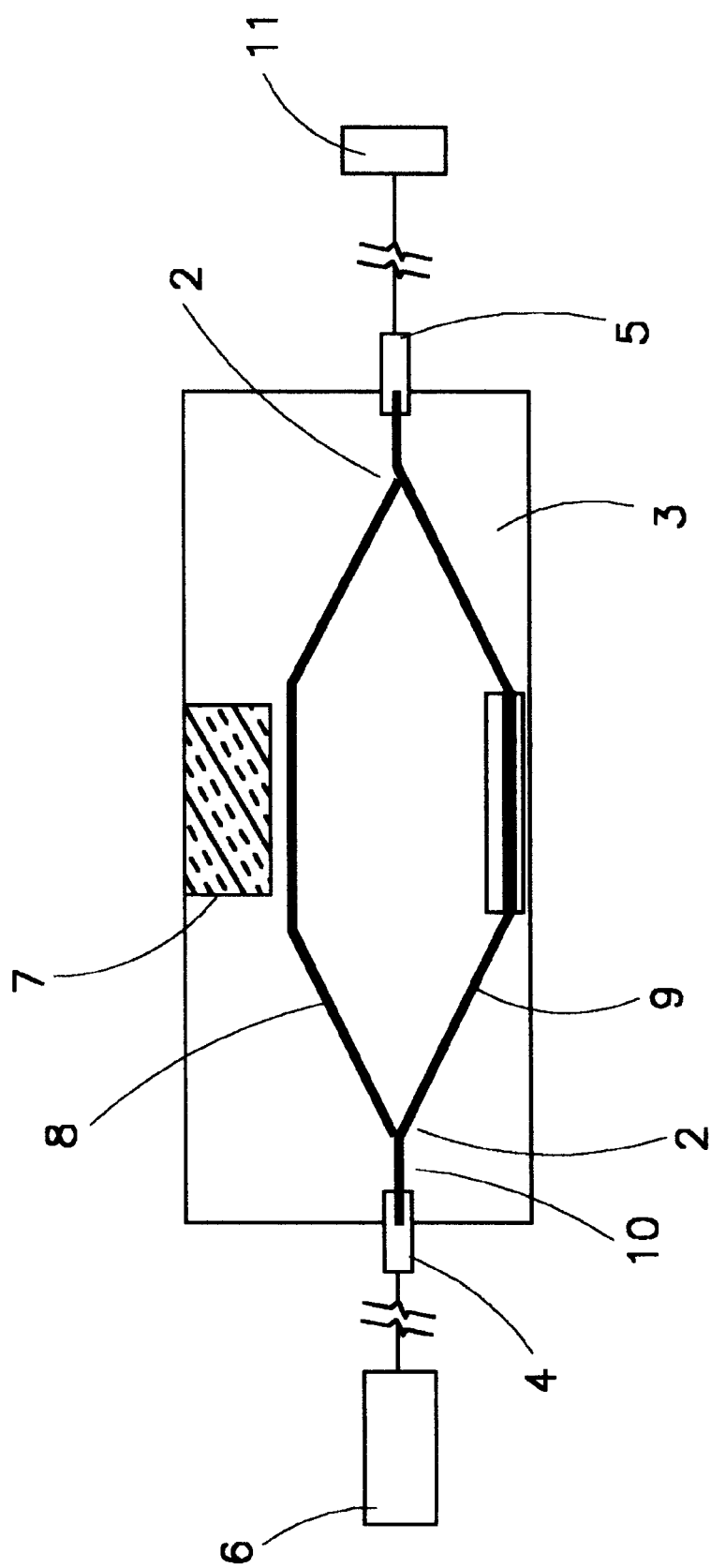
FIG. 1 represents the architecture of a Mach-Zehnder micro-interferometer.

Slight variations in the refractive index ($10^{-6}$ to $10^{-5}$) can be detected and quantified using optical interferometry. The integrated configuration that we will be using is the Mach-Zehnder micro-interferometer, the architecture of which is represented in FIG. 1.

The micro-interferometer is made up of two Y junctions (1, 2) micro-machined onto a substrate (3) of silicon. The optical fibre connection (4, 5) (coupling via a V-groove) allows miniaturisation of the optical head and permits measurement in situ and in vivo. The source used will be a diode laser (6). The source beam (10) of the interferometer is divided into a measurement beam (9) and a reference beam (8). The reference beam (8) whose frequency is shifted in phase by an acoustic modulation produced by a piezo-electric transducer (7), recombines with the reference beam (9) on the photodetector (11). The modulation of the reference beam from the interferometer is obtained using a piezo-electric transducer with a thin layer of zinc oxide, deposited close to the guide layer. The deposition of a thin layer of ZnO of thickness 2.5 $\mu$m is achieved by sputtering. The surface acoustic waves are generated by an interdigital transducer made up of two metal electrodes in the form of a comb deposited on the piezo-electric layer. This supplies a beat signal, the phase of which will be modulated by the value to be measured. The acoustic modulation is therefore an active optical heterodyning device which improves the resolution of the measurement and allows access to the phase of the phenomenon to be measured. In order to confine the acoustic wave within the region of the reference arm, an insulation trench is machined with separates the branches of the interferometer.

Figure 2A:
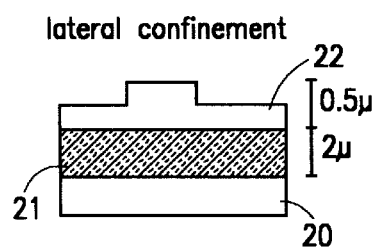
FIGS. 2a and 2b represent section views of two geometries of optical guide.
Figure 2B:
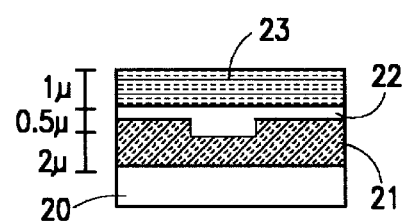

FIGS. 2a and 2b represent section views of two optical guide geometries. The optical guide has a substrate (20) with a thickness of 2 $\mu$m and a refractive index n=1.454 on which is deposited an insulating layer (21), a core (22) of thickness 0.5 $\mu$m made of SiON and possibly cladding (23) of thickness 1 $\mu$m of silicon oxide. In order to benefit from the advantages of silicon technology, the optical guide has a multi-layer structure of the silicon/SiO$_2$/SiON/SiO$_2$ substrate type. It has a refractive index difference of $D_n$=0.066 between the guide layer of SiOH and the adjacent SiO$_2$ layers. The lower layer of SiO$_2$ constitutes insulation between the core of the guide and the silicon substrate and the upper layer can possibly play the role of cladding. The two optical guide structures are produced by LPCVD deposition (possibly PECVD) of the SiO$_2$ and SiOH layers. FIG. 2(a) represents the structure of the "rib" guide and FIG. 2(b) illustrates the structure of the "inverted rib" guide. A jump in index necessary to laterally confine the guided wave is provided respectively by RIE etching of the upper SiOH layer ("rib") and of the lower SiO$_2$ layer ("inverted rib").

The measurement device will be made sensitive to the presence of a specific chemical substance thanks to the deposition on the measurement arm (9) of the interferometer of an upper "superstrate" layer which when it contacts the liquid to be detected will modify the refractive index of this "sensitive" window. Such a variation in the index causes modification of the effective refractive index of the optical guide and produces a variation in optical path, made apparent by a fringes shift. The sensitivity of the measurement is directly proportional to the length of the sensitive window. When contacting the liquid to be measured, the effective refractive index of the guided structure will be modified by an amount $n_{eff}$ that causes a modulation of the interference signal such that $$\frac{I(\Delta\Phi)}{I_0} = \frac{1}{2}\left[1 + \cos\left(\frac{2\pi}{\lambda} \cdot L\Delta n_{eff}\right)\right]$$

where I( ) is the light intensity of the interference pattern, is the wavelength of the incident light wave and L represents the length of the sensitive window.

The originality of the invention is to produce a quantitative and only slightly invasive measurement of the capillary permeability of the small bronchia in vivo, with a technique applicable to man. In practice, the miniaturised sensor, situated at the bronchial opening (previously filled with liquid) allows continuous measurement of the diffusion of a fluorescent indicator from the circulation towards the bronchial opening. This should allow us to develop a quantification of the bronchial capillary permeability and of the bronchial inflammation. Other biological, pharmacological and medical applications are possible, given the possibility of quantifying the exchange of ions and of numerous proteins using specific fluorescent indicators. The functionalities looked for are the miniaturisation and the improvement in performance at low cost. This is made possible by the fact that the concentration of fluorescent marker to be measured is very low, above all at the start of the measurement, and also by the fact that the equipment used will be expendable.

Another original aspect of the integrated device according to the invention is the piezo-electric transducer (7) that allows the creation of a phase modulated interference signal, which constitutes a new route for the creation of optical heterodyning micro-sensors that can be integrated onto a silicon base. The phase modulation of the reference beam of the interferometer will be obtained thanks to a piezo-electric transducer with a thin layer of zinc oxide deposited close to the guide layer. Zinc oxide has a hexagonal structure and in order to obtain surface acoustic waves, the growth of the layer must be such that the C axis of symmetry of the crystal is orthogonal to the substrate: the direction of energy propagation is then collinear with the direction of propagation of the acoustic wave. The deposition of a thin layer of ZnO is obtained by sputtering. The surface acoustic waves will be generated by an interdigital transducer made up of two comb-like metal electrodes deposited on the piezo-electric layer.

One of the essential elements of the integrated device is the material for the upper "superstrate" layer, appropriate choice of which defines both the sensitivity and the spectral range of the measurement. Polymers with the following optimum optical characteristics are especially suitable:

the refractive index must be less than the refractive index of the guide core (n=1.51) so as to allow lateral confinement of the guided beam. This refractive index must also be as close as possible to the refractive index of the $SiO_2$ layer (n=1.454). This choice also allows to avoid too great a mismatch of index at the guide/sensitive area transition, which can create reflections, the relative variation of the refractive index of the polymer, produced by the contact with the fluorescent marker to be detected, must be as great as possible so as to provide good measurement resolution. The maximum value of the refractive index, achieved by the polymer, must always be less than that of the refractive index of the core of the guide (n=1.51), the polymer must have good selectivity for the fluorescent marker to be detected, the absorption peak of the polymer layer must be situated at about 520 nm.

Figure 3:
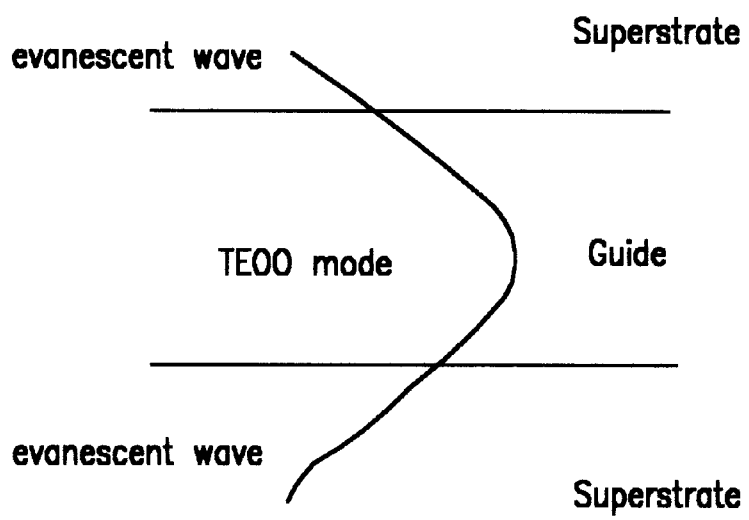
FIG. 3 represents the profile of the guided mode.

FIG. 3 represents the profile of the guided mode.

The combination of two optical guides previously described with reference to the drawings in FIG. 2 with the "sensitive" window of polymer, will confer an original aspect on the measurement device. It should be remembered that in an optical guide, the electrical field which propagates can be broken down schematically into a fundamental mode of order 0 (called TE00) situated at the centre of the core and an evanescent part propagating outside of the core (FIG. 3).

In order to obtain good measurement accuracy the evanescent part of the guided mode must be "favoured" since it remains in contact with the sensitive polymer layer. In effect, one must work with guided modes transporting the energy preferentially in evanescent lines, in order to increase the effect of the external medium on the propagation. Hence high order modes must be used (do not work with mode 0) which propagate more within the cladding than within the core and one must opt for a guide with an "exposed core" at least in the part where the measurement is taking place (sensitive window).

Figure 4A:
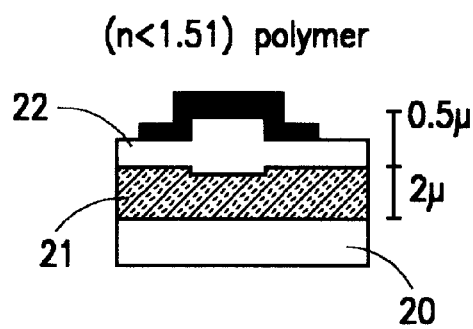
FIGS. 4a and 4b represent two geometries of optical guide with the "superstrate" layer.
Figure 4B:
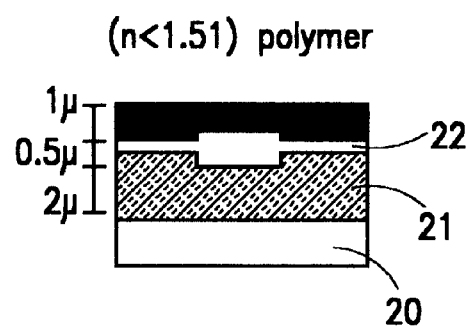

FIGS. 4*a* and 4*b* represent the structure in the "sensitive" region in accordance with two geometries of optical guide with the "superstrate" layer. In the case of the "rib" guide (FIG. 4*a* ) the layer of polymer is deposited directly on the Y junction without the basic structure being modified. This structure is currently used (Reference 4). The deposition is easy to carry out and very long sensitive window lengths can be produced (several centimeters). The principal disadvantage of this configuration is that the core of the guide which is "laid bare" renders the structure sensitive to any modifications of the refractive index from the external environment, since the evanescent line propagates in the free air surrounding the optical guide. Furthermore, in certain biomedical applications where the measurement is carried out in "aggressive" liquids (blood), the exposure of the guide core can provide to be a problem. In the case of the "inverted rib" (FIG. 4*b*) the polymer layer replaces the upper layer of $SiO_2$ in the area of measurement. The guide core is therefore "laid bare" locally and the polymer is used as a "superstrate" for lateral confinement. For this a trench is hollowed out in the upper layer of $SiO_2$ and it is filled with polymer. This original architecture allows one to insulate the guided mode from outside interference. On the other hand the optical losses are very much higher in the polymer (of the order of 3 dB/cm) than in the $SiO_2$ layer (0.1–0.5 dB/cm). An imbalance between the reference arm and the measurement arm of the interferometer is created, that causes there to be a restriction on the size of the sensitive window. This structure is advantageous when one must produce relatively short Y junctions (1–2 cm).

The architecture provided is a Mach-Zehnder interferometer made up of two Y junctions. The technology of the wave guide is multi-layer of the $SiO_2/SiON/SiO_2$ type (a "stripload" type guide).

Figure 5:
FIG. 5 represents a micro-photographic view of one of the Y junctions of the micro-interferometer.

FIG. 5 represents a micro-photographic view of one of the Y junctions of the micro-interferometer.

Figure 6:
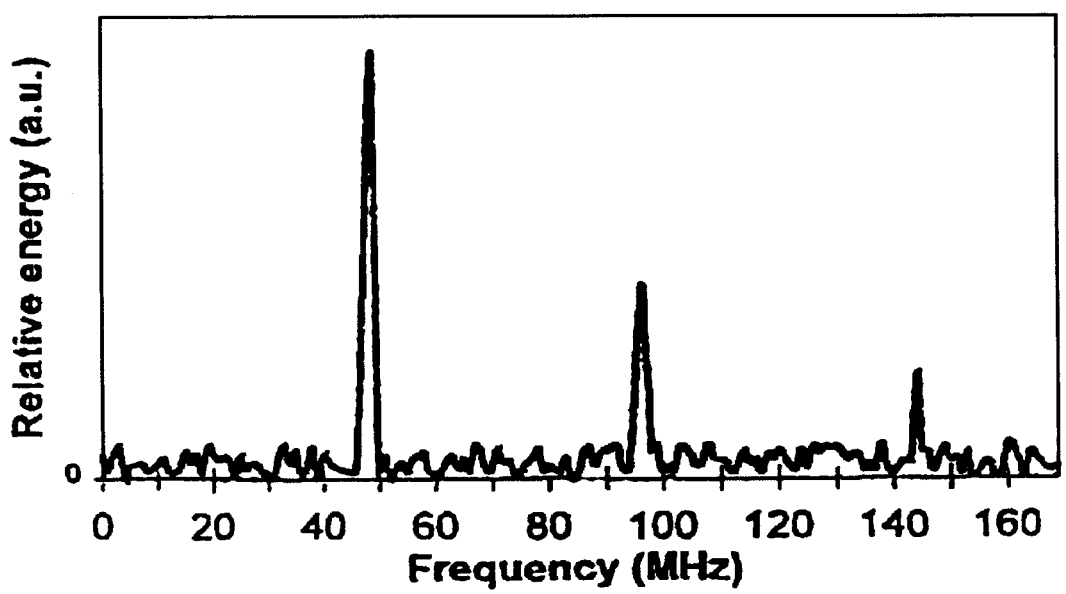
FIG. 6 represents the spectrum of the interference signal.

In the presence of the acoustic modulation, the interference signal contains beats, the frequency of which is that of the acoustic modulation. This result illustrated by FIG. 6 which represents the spectrum of the interference signal where three different harmonics appear. The order one component is situated at the acoustic carrier frequency (48 MHz) and the secondary orders correspond to whole number multiples of it.

The bronchial-alveolar washing is carried out "to saturation", which allows a sample of washing liquid to be reaspirated:

that is representative of the whole bronchial-alveolar area that has been washed, permits it to be standardised to a quantified alveolar volume by dilution of an indicator added to the liquid instilled.

The indicator used is advantageously a neutral dextran (a macromolecule with no biological activity) already used by man, of molecular weight 70000, onto which a fluorescein isothiocyanate is attached. This dextran is administered as a continuous perfusion into the blood for one hour while one proceeds with a bronchial alveolar washing sequentially during the course of the second half hour.

What is claimed is:

1. A sensor for measuring diffusion of a fluorescent marker in cavities, the sensor comprising a Mach-Zehnder micro-interferometer having a reference arm and a measurement arm, wherein the reference arm has a deposit of a sensitive layer whose refractive index is modified when the sensitive layer is in contact with the fluorescent marker, a diode laser configured to generate a source beam, a substrate of silicon micro-machined with two Y junctions, wherein a first Y junction is configured to divide the source beam into a measurement beam along the measurement arm and a reference beam along the reference arm, a piezo-electric transducer configured to shift the frequency of the reference beam in phase by an acoustic modulation, wherein a second Y junction combines the measurement beam and the shifted reference beam to generate a combined beam, and a photodetector configured to detect the combined beam.

2. The invention of claim 1, wherein the measurement and reference arms are made of multi-layer wave guides of the $SiO_2/SiOH/SiO_2$ type.

3. The invention of claim 2, wherein the micro-interferometer has a sensitive window of length L that permits contact of a marked liquid with the measurement arm.

4. The invention of claim 3, wherein the sensitive layer comprises a polymer.

5. The invention of claim 4, wherein the measurement arm has a layer of polymer deposited directly into a Y junction on the core of a wave-guide.

6. The invention of claim 4, wherein the measurement arm has a layer of polymer that replaces an upper insulating layer of $SiO_2$ in a measurement area.

7. The invention of claim 2, wherein the sensitive layer comprises a polymer.

8. The invention of claim 7, wherein the measurement arm has a layer of polymer deposited directly onto a Y junction on the core of a wave-guide.

9. The invention of claim 7, wherein the measurement arm has a layer of polymer that replaces an upper insulating layer of $SiO_2$ in a measurement area.

10. The invention of claim 1, wherein the micro-interferometer has a sensitive window of length L that permits contact of a marked liquid with the measurement arm.

11. The invention of claim 10, wherein the sensitive layer comprises a polymer.

12. The invention of claim 11, wherein the measurement arm has a layer of polymer deposited directly onto a Y junction on the core of a wave-guide.

13. The invention of claim 11, wherein the measurement arm has a layer of polymer that replaces an upper insulating layer of $SiO_2$ in a measurement area.

14. The invention of claim 1, wherein the sensitive layer comprises a polymer.

15. The invention of claim 14, wherein the measurement arm has a layer of polymer deposited directly onto a Y junction on the core of a wave-guide.

16. The invention of claim 14, wherein the measurement arm has a layer of polymer that replaces an upper insulating layer of $SiO_2$ in a measurement area.

* * * * *